SUGAR CANE
Filed Oct. 22, 1963 3 Sheets-Sheet 1
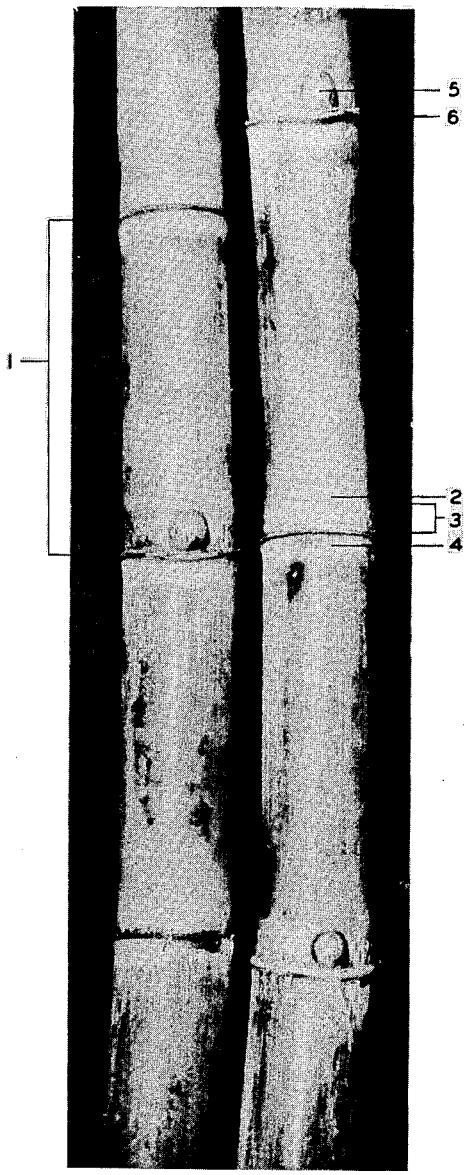
FIG. I
INVENTORS
LESLIE M. WEETMAN
BY BENJAMIN A. BOURNE
Cushman, Darby & Cushman
ATTORNEYS SUGAR CANE
Filed Oct. 22, 1963 3 Sheets-Sheet 2
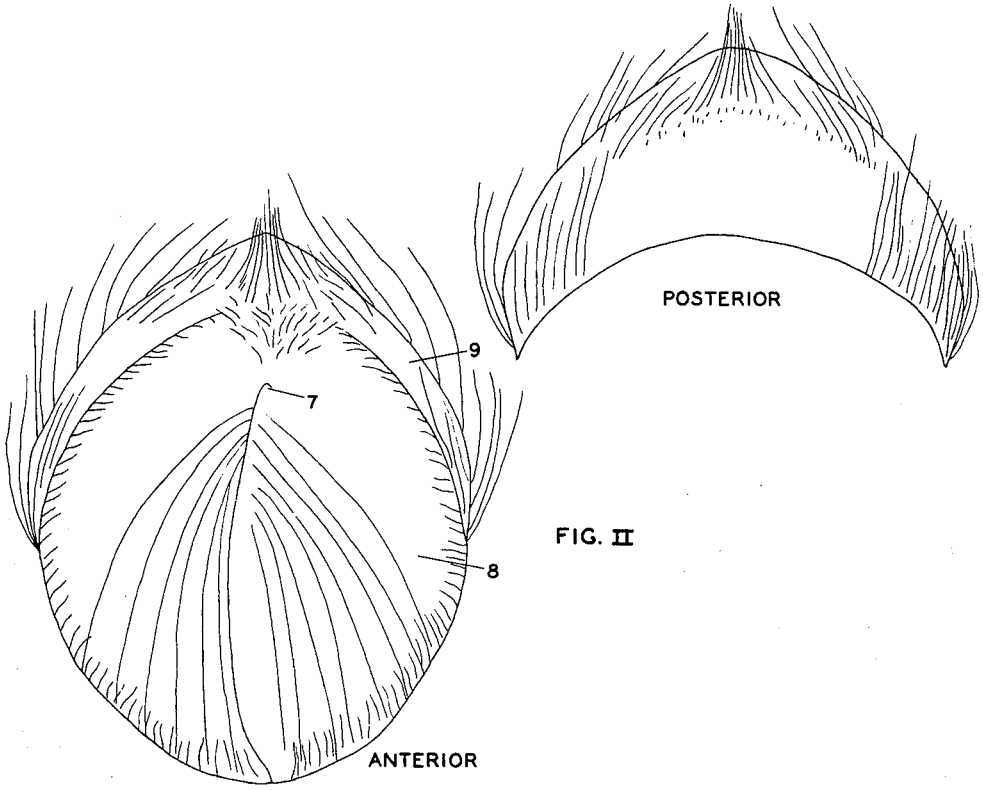
FIG. II
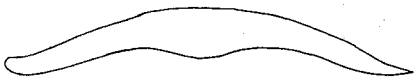
FIG. IV
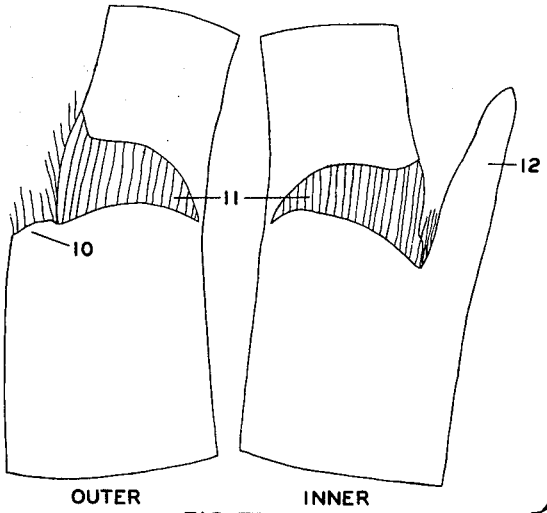
FIG. III
INVENTORS
LESLIE M. WEETMAN
BY BENJAMIN A. BOURNE
Cushman, Darby & Cushman
ATTORNEYS SUGAR CANE
Filed Oct. 22, 1963 3 Sheets-Sheet 3
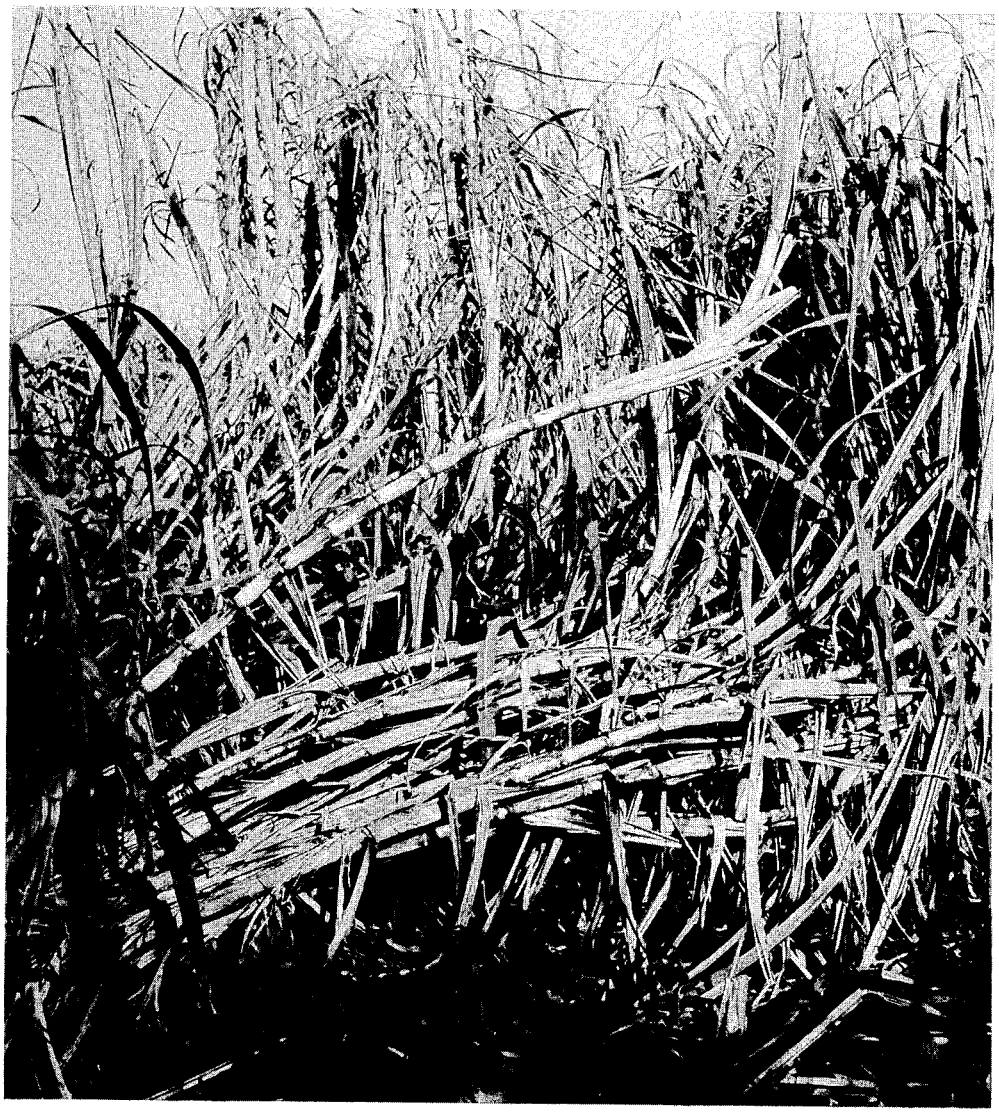
FIG. V
INVENTORS
LESLIE M. WEETMAN
BY BENJAMIN A. BOURNE
Cushman, Darby & Cushman
ATTORNEYS United States Patent Office Plant Pat. 2,511
Patented May 11, 1965

2,511
SUGAR CANE

Leslie M. Weetman and Benjamin A. Bourne, Clewiston, Fla., assignors to United States Sugar Corporation, Clewiston, Fla., a corporation of Delaware Filed Oct. 22, 1963, Ser. No. 318,132
1 Claim. (Cl. Plt.—89)

This new variety of sugar cane originated as a seedling produced by the inventors by crossing the variety Cl. 41–142 as female and the variety Cl. 47–83 as male. (In this form of variety designation, which is well known to sugar cane breeders, "Cl" denotes the breeding locality or station, i.e. Clewiston, Florida; "47" represents the year that the particular variety was first grown, i.e. 1947; and "83" is the distinctive number assigned to that variety among those grown in that year.) The cross was made in December 1953, at Clewiston, Florida, and this new variety was selected from among the progeny of the cross. The inventors have subsequently propagated the variety at Clewiston, Florida, by means of stem cuttings under the identifying number Cl 54–378.

In a replicated variety trial extending over three crop years, juice analyses were made in early November and again in January or February each year. Average indicated yields of 96° sugar per ton of can were 244 pounds for the November analyses and 239 pounds for the January-February analyses. These data indicate very early maturity and high sucrose content over a long possible harvest period. This variety is also vigorous and produces a high tonnage of cane per acre.

Our new variety was planted in a relatively cold area in August 1962. In December it was subjected to killing freezes whereby all above-ground parts of the cane were killed. Subsequently the variety grew up again to a perfect stand and with unusually good vigor and stooling, indicating that it is highly resistant to winter killing.

Ratoon stunting disease being an important factor in sugar production from sugar cane, a series of comparative studies was made by means of randomized block field tests with this variety, replicated five times, to determine the effect of hot air heat treatment at 50° C. for 24 hours of propagating stalk material for the purpose of eliminating the ratoon stunting virus. The non-heated stalk material was inoculated with the RSD virus by soaking cuttings in the freshly expressed juice of a heavily diseased variety. The tests were run for both plant cane (1st crop) and as first stubble crop cycles. A statistical analysis of the data showed that even when 100% infected, no significant reduction in cane tonnage per acre resulted during both crop cycles when harvested toward the middle or late periods of the usual cane grinding season (January 22 to March 1st). If harvested early in mid November, however, the heat treated, RSD free cane was found to produce significantly less sugar per ton of cane amounting to an average of 25.8 lbs. as plant cane. By delaying harvest until mid January this depreciation in quality disappeared. That the quality depreciation in heat treated disease-free cane affected the 1st stubble was thoroughly demonstrated by the fact that even as late as January 7th, the significant loss of sugar per ton amounted to 3.8 lbs. In the absence of severe early freezing weather, harvesting in late January at mid normal grinding period showed no significant differences in yields of sugar per acre whether the cane was 100% diseased or disease-free, following heat treatment. However, it was discovered that if the first stubble cane became frozen in mid December, subsequent non-heat treated diseased cane suffered a 27.3% reduction in percent yield of 96° sugar after a lapse of 44 days, whereas the plots heat treated for RSD elimination suffered a percent yield reduction in 96° sugar of only 5.7 percent. In view of this advantage in rate of deterioration, heat treatment for RSD control is recommended for use in cold marginal areas where deterioration in quality after freezing is a problem. For early harvesting purposes, heat treatment for RSD control is not recommended because of the severe reduction in cane quality and inadequate response for increased cane tonnage.

Repeated tests have been made to determine the resistance or susceptibility of this variety to the four strains of mosaic virus which occur in south Florida, viz. "A," "B," "D" and "E." In one test, for example, 36 plants were inoculated by the air-brush artificial technique with a potent mixture of all the above four strains. Not a single plant became infected after an incubation period of 73 days, whereas the control variety showed 50% of the 18 inoculated plants diseased after this period. A 40′ planting of this new variety exposed in the field to natural infection by all four mosaic strains for a two-year period has remained free of infection. It has been concluded, therefore, that the new variety is at present immune to the existing strains of mosaic virus in Florida.

In the drawings:

FIGURE I is a photographic view of approximate mid-sections of typical stalks, showing internode 1, stem bud 5, growth ring 2, leaf scar 6, wax ring 4, and root band 3;

FIGURE II shows anterior and posterior views of the stem bud, showing germ pore 7, prophyll 8, and wing 9;

FIGURE III is a view of the two separated and flattened halves of the upper part of a leaf sheath, showing the outer auricle 10, the inner auricle 12 and the dewlap or blade joint 11;

FIGURE IV is a view showing the outline of a ligule after its removal from the inner surface of the leaf sheath; and FIGURE V is a photographic view showing the habit of growth of mature cane.

DETAILED DESCRIPTION

In the following detailed description of the new variety of sugar cane, the terminology employed in morphological description and numbering of hair groups is that employed by Artschwager. (See Sugarcane (*Saccharum officinarum* L.): Origin, Classification, Characteristics, and Description of Representative Clones by Ernst Artschwager and E. W. Brandes. Agriculture Handbook No. 122. United States Department of Agriculture, 1958.) Color descriptions are made by referring to the plates of Maerz and Paul. (See A Dictionary of Color, second edition, by A. Maerz and M. Rea Paul. McGraw-Hill Book Company, 1950.)

*The stalk (or culm)*

*Habit of growth* (see FIGURE V).—Stalks are at first erect, but they usually become recumbent in mature cane. The internodes are straightly aligned.

*Size.*—The stalks are usually 10 or more feet in length, averaging 123 inches. They are nearly circular in cross-section, averaging 27.9 x 29.2 millimeters in the middle part of the stalk. The larger diameter may vary from 26 to 33 millimeters.

*Flesh.*—The color of the flesh is approximately Maerz and Paul's designation 11–H–2. The flesh is solid. Fiber content averages 11.45%.

*Internodes* (1, FIGURE I).—They are nearly cylindrical in shape and are 11 to 18 centimeters long in the middles of the stalks, averaging 12.5 centimeters. Some internodes have no bud furrows; others have slight grooves one-half to three-fourths the length of the internode. Corky cracks or growth cracks are not evident.

*Color.*—The basic color just above the growth ring on unexposed internodes is just a little deeper than Maerz and Paul's 19–G–1. Exposed portions of the stalk turn reddish brown where not covered with mold growth. Freshly stripped stalks give an appearance of yellow-green splotched with gray-black (from mold growth). The wax ring (4, FIGURE I) is moderately heavy and forms a distinct line of demarcation with the rather light bloom on the remainder of the internode.

*Growth ring* (2, FIGURE I).—It is 1 to 2 millimeters in height and slightly tumescent. The color at first approximates Maerz and Paul's designation 12–I–5, but usually turns green in the sunlight.

*Root band* (3, FIGURE I).—It is straight on the bud side and obconoidal opposite the bud. It is 7 to 9 millimeters tall, being taller on the bud side. The color is slightly lighter than the basic color of the internode but turns green when exposed to sunlight. There are 4 rows of root primordia, but these may vary in number, and the number of rows may not always be distinct.

*Leaf scar* (6, FIGURE I).—The leaf scar protrudes and is slightly oblique, being tilted under the bud.

*Epidermal cells.*—The pattern of the stem epidermal cells is basically Artschwager's type 1 in which the small cell groups consist of one cork cell and one silica cell in single pairs. However, there are a considerable number of groups which consist of two cork cells and one silica cell, as in type 7. Also, there are a number of cork cells with pointed ends, as in type 4; finally there are a few cell groups consisting only of a single cork cell, as in type 3. This combination would be designated as pattern 1+7+4+3 in Artschwager's system. There are about 605 short cell groups per square millimeter, and the long cells average 11.3 microns in width. Stomata are present and average 6.4 per square millimeter.

*Stem buds*

*General characteristics.*—The buds (5, FIGURE I) are inserted at or slightly above the edge of the leaf scar. The tips usually extend to the growth ring. The buds are not protruding nor overly prominent and have an average size of about 8.6 millimeters wide by 10.1 millimeters tall. The prophyll (8, FIGURE II) is oval in shape with round tip.

*Wings of the prophyll* (9, FIGURE II).—The wings are inserted at or slightly below the middle of the prophyll and are medium broad, broader near the tip.

*Pubescence.*—The buds are more or less heavily fringed with long hairs. Hair groups 1, 2, 4, 10, 11, 14, 16, 19, 22, 26, and 29 are usually prominent.

*The leaf*

*The blade.*—The blades are spreading and curved. They are medium dark green in color. The larger leaves on each stalk are 5 to 7 centimeters wide, averaging 6.5, and are 130 to 175 centimeters wide, averaging 157. The ratio of the length of the blade to the width thereof averages 24.4.

*The sheath.*—The sheaths have an average length of 34 centimeters. The older ones adhere moderately to the stalks. The dorsal field of pubescence (group 57) is large, extending about three-fourths of the length of the sheath. It is pointed at each end but broadens rapidly to cover most of the width of the sheath and coalesces with the lateral fields. The hairs are moderately dense and long and are mostly appressed and spinelike. They are often deciduous on older sheaths. The lateral fields (group 60) are often present near both margins and are distinct from the dorsal field for about 8 centimeters on the upper margins of the sheath. They are about 10 millimeters wide, and the hairs are rather dense.

*Dewlaps* (11, FIGURE III).—The color of the dewlaps varies from about Maerz and Paul's designation 14–J–2 (silver fern) to 15–H–1. The shape is approximately flaring double-crescent. The outer surface of the dewlap is covered with dense felt-like hairs of group 58, which are somewhat longer than in many clones. Group 58*a* is not present. The outer surface is covered with a moderate layer of wax. The inner surface has a rather conspicuously hairy appearance, being entirely covered with a dense mat of fairly long hairs of group 52, which also extends across the midrib. Groups 55 and 63 are also present on the midrib. Group 65 is apparently not present. There are tufts of long hairs of group 51 on the outer margins of the dewlap.

*Auricles.*—The outer auricle (10, FIGURE III) is straight transitional to somewhat ascending in shape and varies from 0 to 6 millimeters in height. The inner auricle (12, FIGURE III) is usually lanceolate, but it may be deltoid or even transitional on the higher sheaths. The lanceolate auricles vary from 11 to 42 millimeters in length. There is a prominent tuft of long hairs on the outer auricle and at the base of the inside margin of the inner auricle.

*Ligules* (FIGURE IV).—The ligule is broadly crescent-shaped with broad lozenge. It is 6 to 7 millimeters tall. The upper margin of the ligule is uneven, giving a jagged appearance under magnification. The marginal cilia average about ½ millimeter in length. The dorsal surface of the ligule is covered with long appressed hairs.

*Inflorescence.*—This new variety flowers only infrequently in Florida.

Important characteristics which, in combination, help to distinguish this new variety of sugar cane from all other known varieties are:

(1) Very early maturity.

(2) High sucrose content over a long possible harvest period.

(3) Ability to grow back vigorously after freezing of above-ground parts.

(4) High resistance to or tolerance of the ratoon stunting disease, making heat treatments generally unnecessary.

(5) Immunity to strains "A," "B," "D," and "E" of sugar cane mosaic virus both by natural and artificial means of transmission in south Florida.

(6) Stalks which usually become recumbent in mature cane.

(7) Stalks with diameters in the middle parts of the stalks averaging about 27.9 x 29.2 millimeters.

(8) Fiber content of stalks averaging about 11.45%.

(9) Shallow bud furrows present on some of the internodes.

(10) Growth ring averaging 1 to 2 millimeters tall.

(11) Root band usually 7 to 9 millimeters tall with usually 4 rows of root primordia, but the number of rows may be indistinct.

(12) The stem epidermal pattern is type 1+7+4+3 in Artschwager's terminology.

(13) Stomata present in the stem epidermis.

(14) The prophyll of the stem bud is oval in shape.

(15) The wing is inserted at or slightly below the middle of the prophyll.

(16) The buds are rather prominently fringed with hairs.

(17) The dorsal pubescence of the leaf sheath covers a broad area, and the hairs are spinelike.

(18) The dewlaps are flaring double-crescent in shape.

(19) The inner surface of the dewlap is entirely covered with a dense mat of hairs which extends across the midrib.

(20) The outer auricle is usually straight transitional in shape.

(21) The inner auricle is usually lanceolate in shape.

(22) The ligule is broadly crescent-shaped with broad lozenge and is usually about 6 or 7 millimeters tall.

(23) The marginal cilia of the ligule average about ½ millimeter in length.

What is claimed is:

The new and distinct variety of sugar cane herein shown and described, identified by the combination of the characteristics enumerated above.

No references cited.

ABRAHAM G. STONE, *Primary Examiner.*